(12) United States Patent
Sommer et al.

(10) Patent No.: US 8,340,783 B2
(45) Date of Patent: Dec. 25, 2012

(54) IMPLANTABLE MEDICAL DEVICE LEAD WITH SELECTIVELY EXPOSED ELECTRODES AND REINFORCEMENT MEMBER

(75) Inventors: John L. Sommer, Coon Rapids, MN (US); Kenneth C. Gardeski, Plymouth, MN (US); Xiaonan Shen, Shoreview, MN (US); Jon D. Schell, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 106 days.

(21) Appl. No.: 12/825,647

(22) Filed: Jun. 29, 2010

(65) Prior Publication Data

US 2010/0331938 A1 Dec. 30, 2010

Related U.S. Application Data

(60) Provisional application No. 61/221,960, filed on Jun. 30, 2009.

(51) Int. Cl.
*A61N 1/05* (2006.01)

(52) U.S. Cl. ........................................ 607/116; 607/122

(58) Field of Classification Search .................. 607/116, 607/117, 119, 122, 125, 126
See application file for complete search history.

(56) References Cited

U.S. PATENT DOCUMENTS

| | | | |
|---|---|---|---|
| 5,545,203 A | 8/1996 | Doan | |
| 5,578,067 A | 11/1996 | Ekwall et al. | |
| 5,713,944 A | 2/1998 | Kroll | |
| 5,824,030 A | 10/1998 | Yang et al. | |
| 5,919,222 A | 7/1999 | Hjelle et al. | |
| 6,556,873 B1 | 4/2003 | Smits | |
| 6,606,522 B2 * | 8/2003 | Schell | 607/122 |
| 7,212,867 B2 | 5/2007 | Van Venrooij et al. | |
| 2002/0183817 A1 * | 12/2002 | Van Venrooij et al. | 607/116 |
| 2004/0176782 A1 * | 9/2004 | Hanse et al. | 606/129 |
| 2004/0199069 A1 * | 10/2004 | Connelly et al. | 600/412 |
| 2006/0089695 A1 | 4/2006 | Bolea et al. | |

OTHER PUBLICATIONS

U.S. Appl. No. 61/221,960, filed Jun. 30, 2009, entitled Implantable Medical Device Lead, by John L. Sommer, et al.

* cited by examiner

*Primary Examiner* — Carl H Layno
*Assistant Examiner* — Eugene Wu
(74) *Attorney, Agent, or Firm* — Reed A. Duthler; Stephen W. Bauer

(57) ABSTRACT

An implantable lead including a lead body including an outer surface, a proximal end, a distal end, and at least one electrode; an electrically insulating member that extends axially over a first portion of the outer surface of the lead body between the proximal end and distal end, the electrically insulating member defining at least one aperture that exposes a first portion of the at least one electrode when in a first position over the lead body; and a reinforcement member formed at least partially of a different material than the insulating member and coupled to the insulating member, the reinforcement member extending axially over the outer surface of the lead body between the insulating member and proximal end. The reinforcement member may be configured to transfer at least one of a radial or axial force from a proximal portion of the reinforcement member to the insulating member, wherein the at least one of radial or axial force transferred to the insulating member is sufficient to move the insulating member over the outer surface of the lead body. In some examples, the lead may further include a deployable lobe member configured to anchor the reinforcement member and insulating member adjacent a tissue site within a patient.

13 Claims, 10 Drawing Sheets

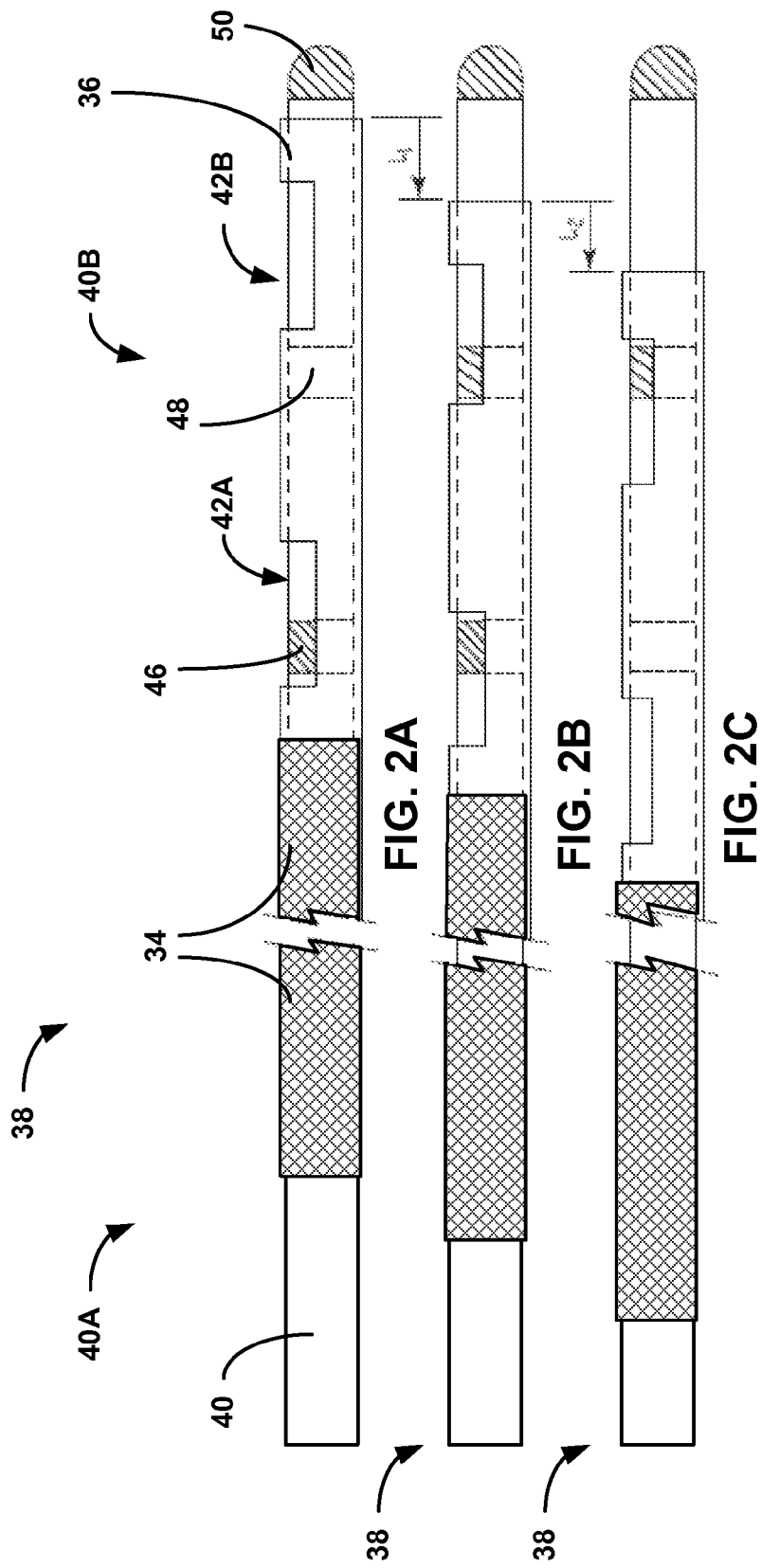

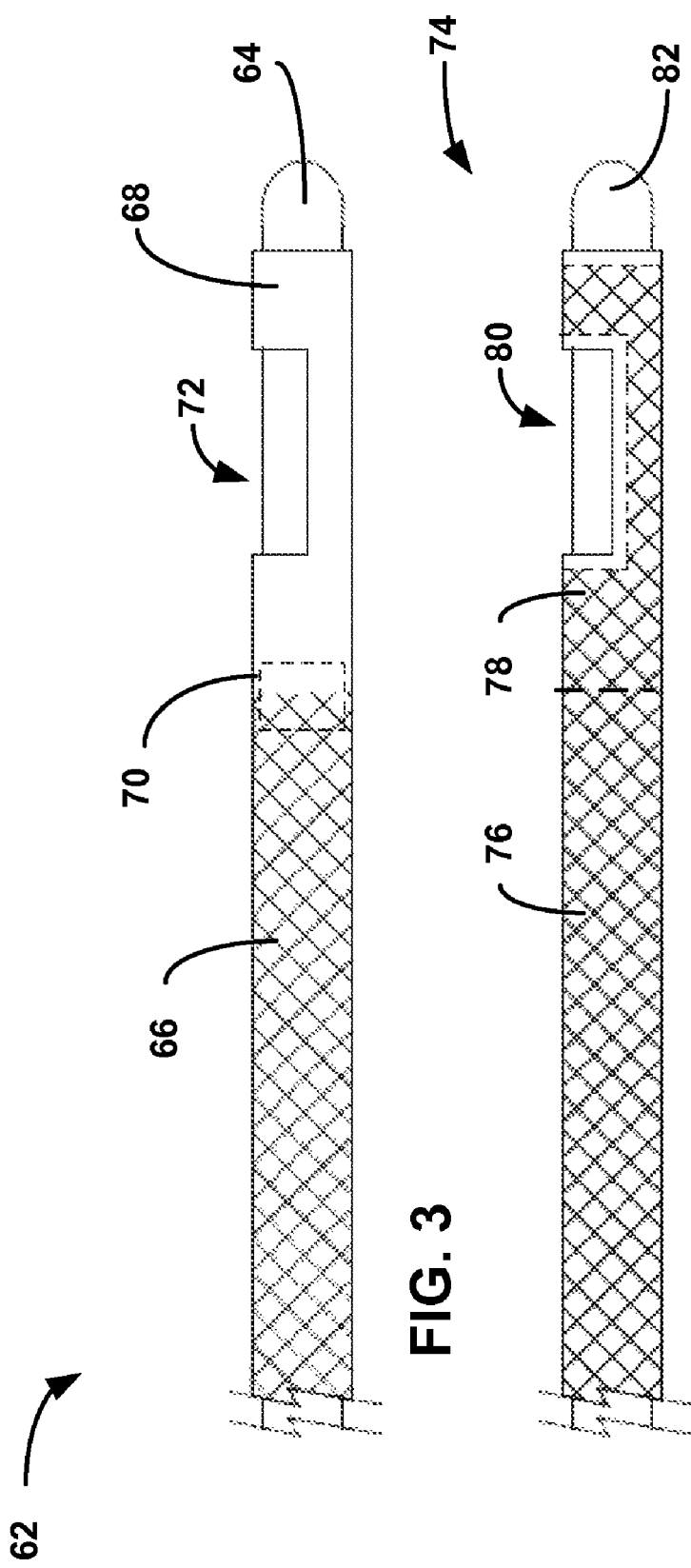

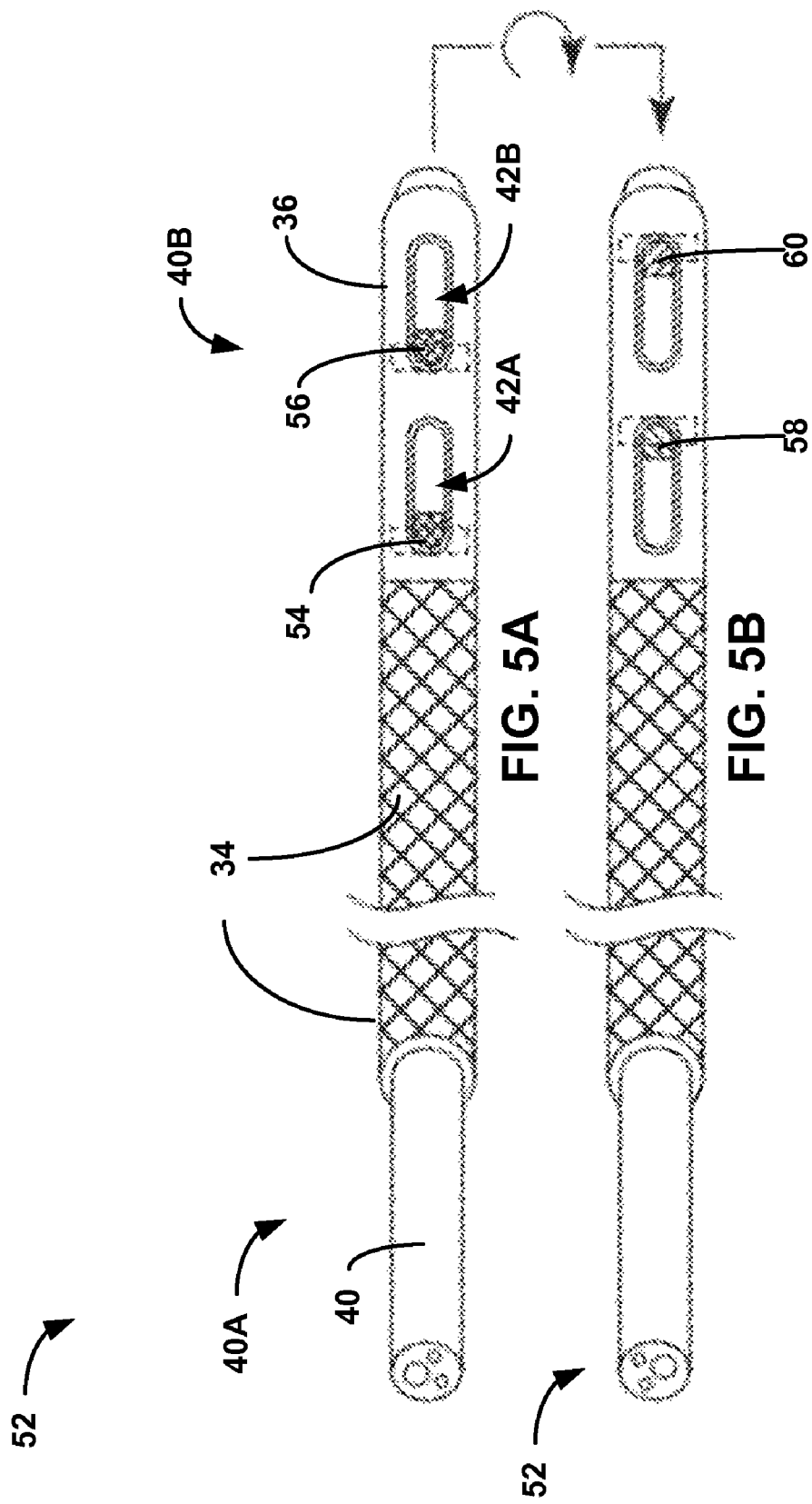

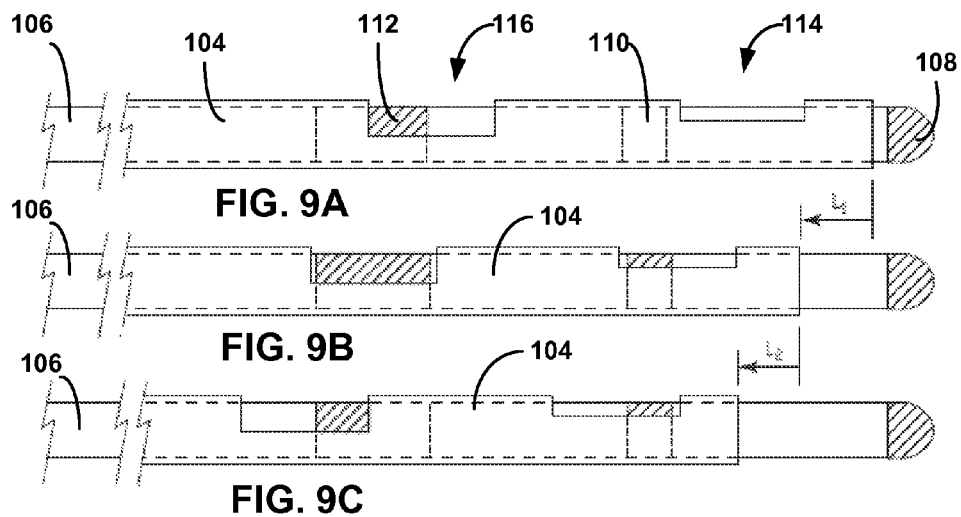
FIG. 9A
FIG. 9B
FIG. 9C
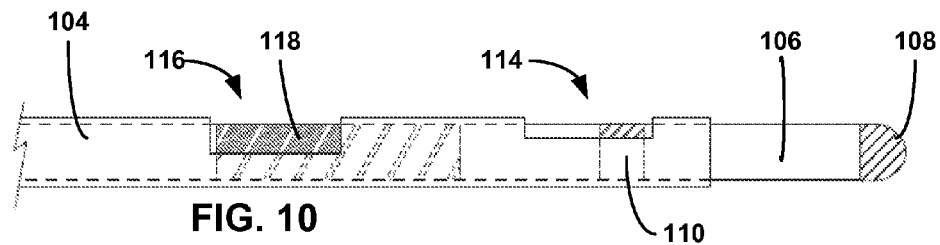
FIG. 10

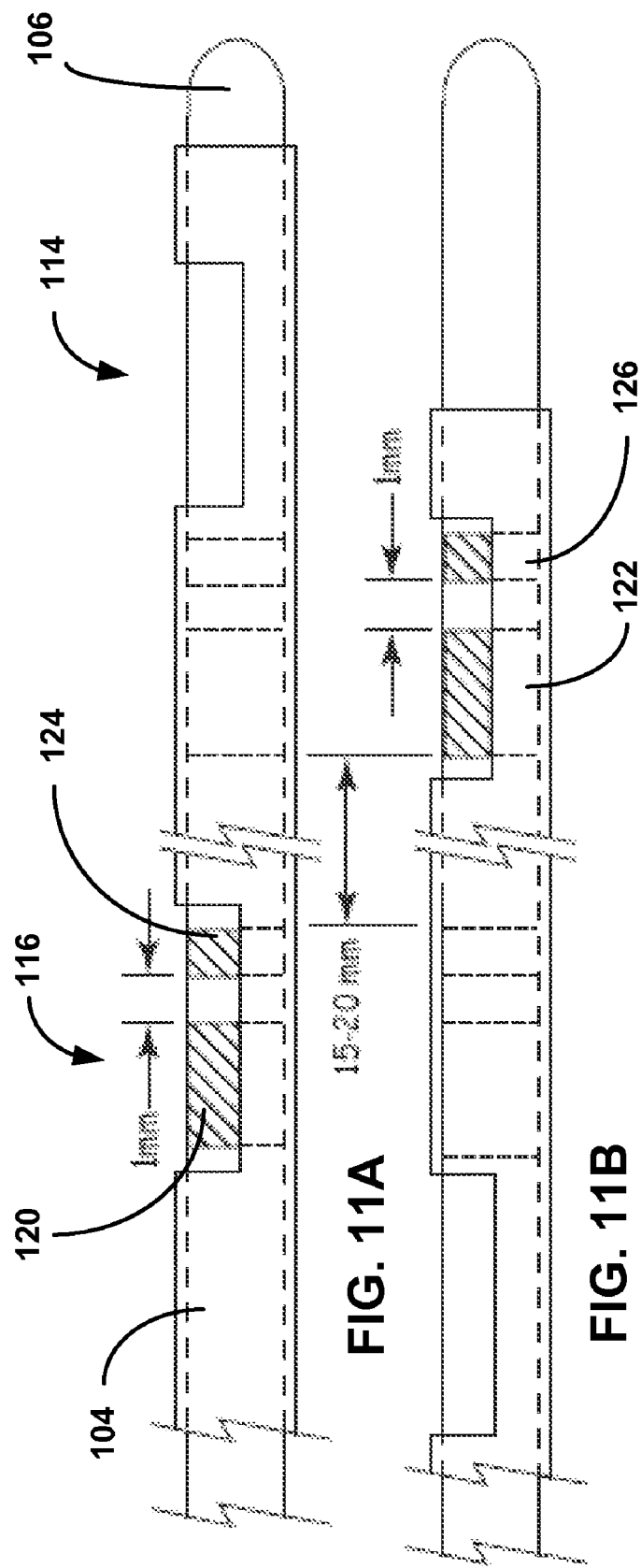

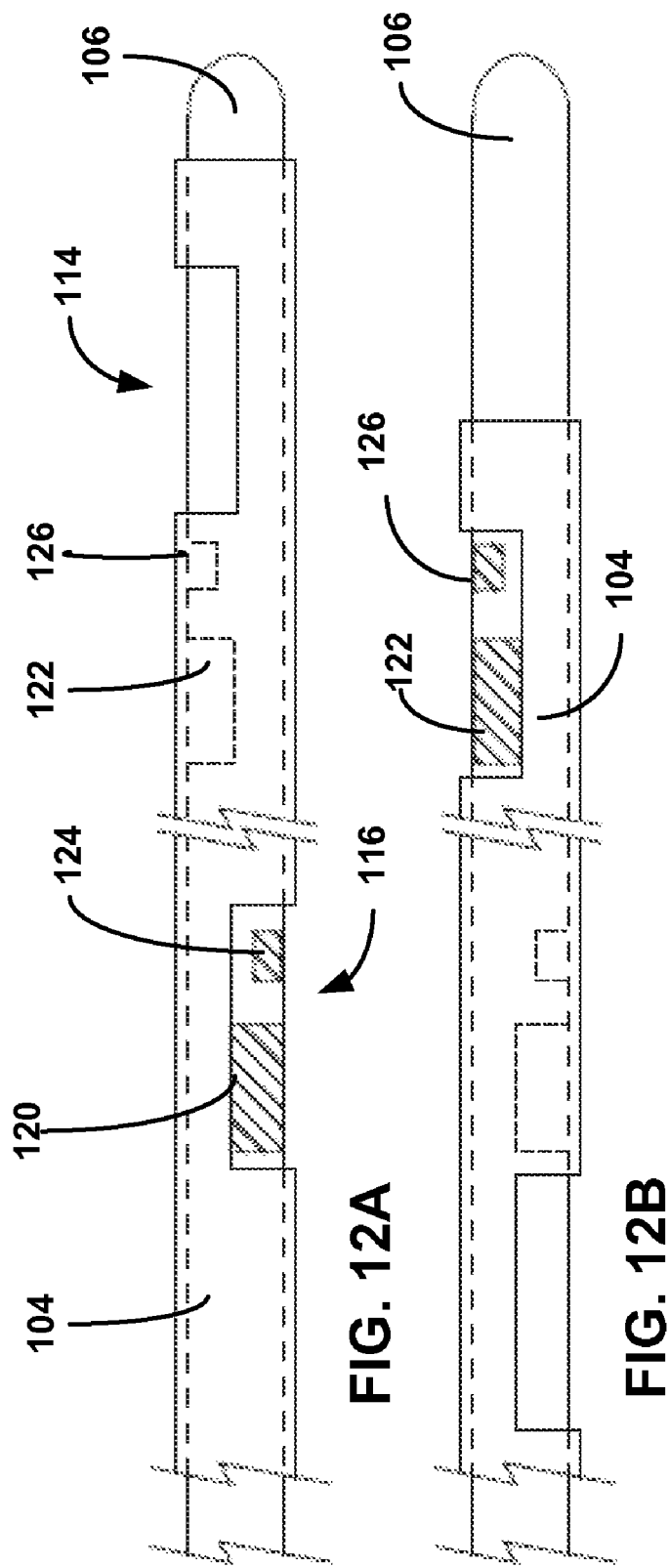

IMPLANTABLE MEDICAL DEVICE LEAD WITH SELECTIVELY EXPOSED ELECTRODES AND REINFORCEMENT MEMBER

This application claims the benefit of U.S. Provisional Application No. 61/221,960, entitled, "IMPLANTABLE MEDICAL DEVICE LEAD," and filed on Jun. 30, 2009, the entire content of which is incorporated herein by reference.

TECHNICAL FIELD

The disclosure relates to medical devices and, in particular, implantable medical devices configured to deliver electrical stimulation therapy to a patient.

BACKGROUND

A wide variety of implantable medical devices ("IMD") that deliver therapy to or monitor a physiologic condition of a patient have been clinically implanted or proposed for clinical implantation in patients. Some implantable medical devices may employ one or more elongated electrical leads and/or sensors. Such implantable medical devices may deliver therapy or monitor the heart, muscle, nerve, brain, stomach or other organs. In some cases, implantable medical devices deliver electrical stimulation therapy and/or monitor physiological signals via one or more electrodes or sensor elements, which may be included as part of one or more elongated implantable medical leads. Implantable medical leads may be configured to allow electrodes or sensors to be positioned at desired locations for delivery of stimulation or sensing electrical depolarizations. For example, electrodes or sensors may be located at a distal portion of the lead. A proximal portion of the lead may be coupled to an implantable medical device housing, which may contain electronic circuitry such as stimulation generation and/or sensing circuitry.

For example, implantable cardiac devices, such as cardiac pacemakers or implantable cardioverter defibrillators, provide therapeutic stimulation to the heart by delivering electrical therapy signals such as pulses or shocks for pacing, cardioversion or defibrillation pulses via electrodes of one or more implantable leads. In some cases, an implantable cardiac device may sense intrinsic depolarizations of the heart, and control the delivery of therapeutic stimulation to the heart based on the sensing. When an abnormal rhythm of the heart is detected, such as bradycardia, tachycardia or fibrillation, an appropriate electrical therapy (e.g., in the form of pulses) may be delivered to restore the normal rhythm. For example, in some cases, an implantable medical device may deliver pacing, cardioversion or defibrillation signals to the heart of the patient upon detecting ventricular tachycardia, and deliver cardioversion or defibrillation therapy to a patient's heart upon detecting ventricular fibrillation.

SUMMARY

In general, the disclosure is directed to medical systems including at least one medical lead, e.g., an implantable medical lead, for delivering electrical stimulation therapy to a patient. The implantable lead may be adapted to be placed within a patient proximate a tissue site targeted for electrical stimulation, and the electrical stimulation may be delivered to the patient via one or more electrodes arranged on a distal a portion of the implantable lead positioned proximate the target tissue site.

The implantable lead includes an insulating member, e.g., a tubular sleeve formed of an electrically insulating material, configured to surround a portion of the outer surface of the lead body adjacent one or more of the lead electrodes. The insulating member may define one or more aperture such that the insulating sleeve may be positioned over the outer surface of the lead body to selectively expose all or portions of the lead electrode(s) by actuating the member in an axial and/or radial direction.

The lead may further include a reinforcement member coupled to the insulating member to facilitate the movement of the insulating member over the lead body, e.g., during the positioning of the insulating member over the lead body within a patient. For example, the reinforcement member may include a tubular sleeve formed of braided structure, such as, e.g., a braided wire structure, that extends from the insulating member positioned near the distal end of a lead to the proximal portion of lead body configured to connect to an implantable medical device ("IMD"). In some examples, the reinforcement member may be configured to shield the lead body from RF fields generated during magnetic resonance imaging (MRI) and/or to provide protection to the lead against compressive forces that may result in lead crush. In some examples, the lead may further includes a deployable lobe member configured to anchor the reinforcement member and insulating member adjacent a tissue site within a patient.

In one example, the disclosure is directed to an implantable lead including a lead body including an outer surface, proximal end, a distal end, and at least one electrode; an electrically insulating member that extends axially over a first portion of the outer surface of the lead body between the proximal end and distal end, the electrically insulating member defining at least one aperture that exposes a first portion of the at least one electrode when in a first position over the lead body; and a reinforcement member formed at least partially of a different material than the electrically insulating member and coupled to the insulating member, the reinforcement member extending axially over the outer surface of the lead body between the insulating member and proximal end, wherein the reinforcement member is configured to transfer at least one of a radial or axial force from a proximal portion of the reinforcement member to the insulating member, and wherein the at least one of radial or axial force transferred to the insulating member is sufficient to move the insulating member over the outer surface of the lead body.

In another example, the disclosure is directed to a method comprising delivering electrical stimulation therapy to a tissue site of a patient from a medical device via a first portion of at least one electrode of a lead, wherein the lead includes a lead body including an outer surface, a proximal end, a distal end, and the at least one electrode; an electrically insulating member that extends axially over a first portion of the outer surface of the lead body between the proximal end and distal end, the electrically insulating member defining at least one aperture that exposes the first portion of the at least one electrode when in a first position over the lead body; and a reinforcement member formed at least partially of a different material than the electrically insulating member and coupled to the insulating member, the reinforcement member extending axially over the outer surface of the lead body between the insulating member and proximal end, wherein the reinforcement member is configured to transfer at least one of a radial or axial force from a proximal portion of the reinforcement member to the insulating member, and wherein the at least one of radial or axial force transferred to the insulating member is configured to move the insulating member over the outer surface of the lead body.

In another example, the disclosure is directed to an implantable lead comprising a lead body including an outer surface, a proximal end, a distal end, and at least one electrode; means for electrically insulating the at least one electrode extending axially over a first portion of the outer surface of the lead body between the proximal end and distal end, wherein the means for electrically insulating includes a means for defining at least one aperture that exposes a first portion of the at least one electrode when in a first position over the lead body; and means for transferring at least one of radial or axial force to the means for electrically insulating the at least one electrode, wherein the means for transferring at least one of radial or axial force is formed at least partially of a different material than the means for electrically insulating the at least one electrode, and wherein the at least one of radial or axial force is sufficient to move the means for electrically insulating the at least one electrode over the outer surface of the lead body.

The details of one or more examples are set forth in the accompanying drawings and the description below. Other features, objects, and advantages of the disclosure will be apparent from the description and drawings, and from the claims.

BRIEF DESCRIPTION OF DRAWINGS

FIGS. 2A-2C are conceptual diagrams illustrating an example lead including an example reinforcement member and example insulating member.

FIG. 3 is a conceptual diagram illustrating a distal portion of an example lead including an example reinforcement member and example insulating member.

FIG. 4 is another conceptual diagram illustrating a distal portion of an example lead including an example reinforcement member and example insulating member.

FIGS. 5A and 5B are conceptual diagrams illustrating an example lead including an example reinforcement member and example insulating member.

FIGS. 9A-9C are conceptual diagrams illustrating an example insulating member.

FIG. 10 is a conceptual diagram illustrating an example insulating member.

FIGS. 11A and 11B are conceptual diagrams illustrating an example insulating member.

FIGS. 12A and 12B are conceptual diagrams illustrating an example insulating member.

DETAILED DESCRIPTION

Figure 1:
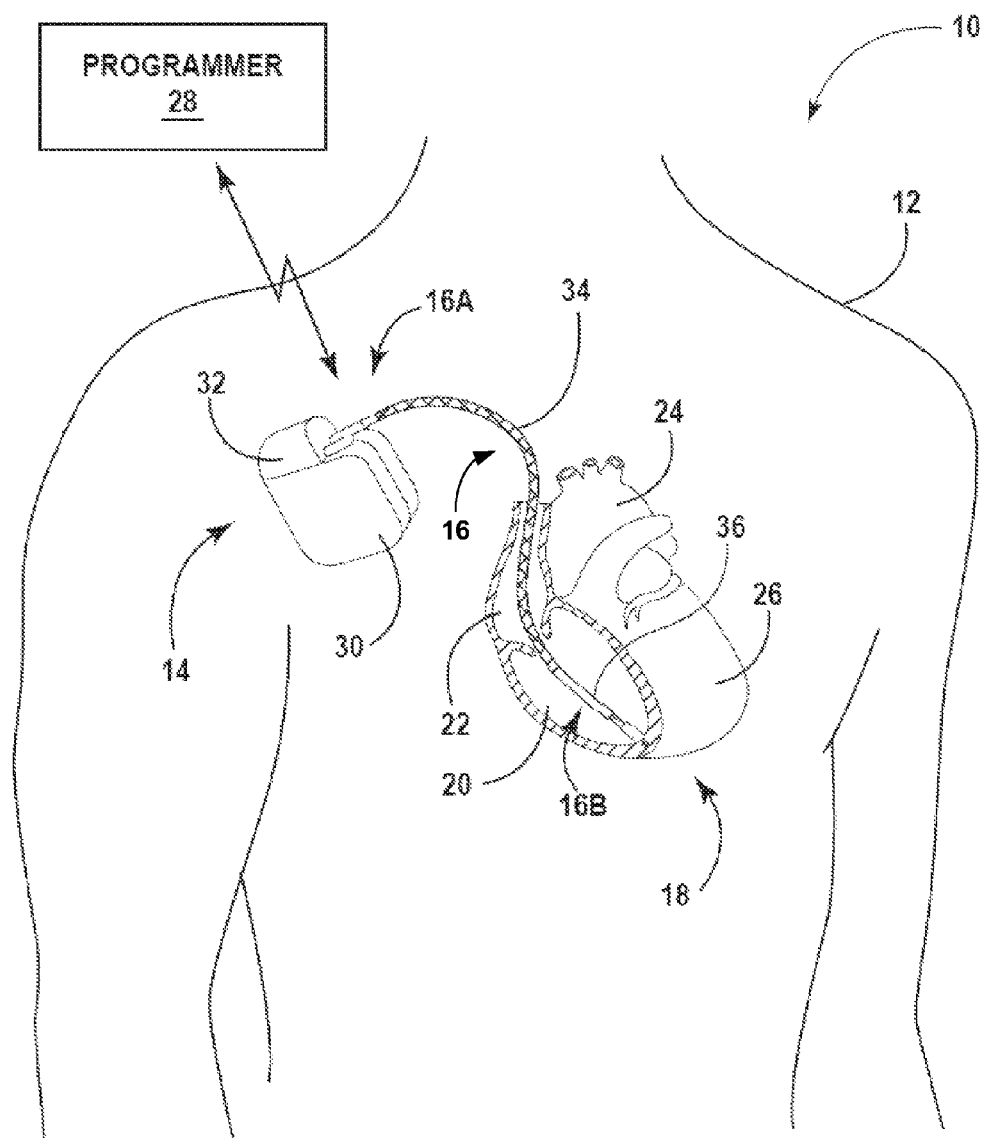
FIG. 1 is a conceptual diagram illustrating an example therapy system that includes an example implantable medical device (IMD) configured to deliver electrical stimulation heart of the patient.

In general, the disclosure is directed to medical systems including at least one medical lead for delivering electrical stimulation therapy to a patient. For example, the medical lead may be an implantable lead adapted to be positioned within a patient adjacent to one or more tissue sites. The implantable lead may deliver electrical stimulation generated by an implantable medical device (IMD) to the target tissue via one or more electrodes arranged on a distal portion of the lead body. The implantable lead may include an insulating member, e.g., a tubular sleeve formed of an electrically insulating material, surrounding a portion of the lead body adjacent one or more of the lead electrodes. The insulating member may define one or more apertures such that the insulating sleeve may be oriented relative to the lead body to selectively expose all or portions of the lead electrode(s) by actuating the member in an axial and/or radial direction.

The implantable lead further includes a reinforcement member coupled to the insulating member to facilitate the movement of the insulating member over the lead body, e.g., during the positioning of the insulating member over the lead body within a patient. For example, the reinforcement member may include a tubular sleeve formed of braided metal wire that extends from the insulating member positioned near the distal end of a lead to the proximal portion of lead body configured to connect to an implantable medical device ("IMD"). In such a configuration, the reinforcement member may be moved radially and/or axially near the proximal portion of the lead body to position the insulating member over the distal portion of the lead body. In some examples, the reinforcement member may be configured to electromagnetically shield the conductors with the lead from RF fields generated during magnetic resonance imaging (MRI) and/or to provide protection to the lead against crush.

In some examples, an implantable lead may be utilized to provide cardiac rhythm management therapy generated by an implantable medical device to the heart of a patient. The proximal end of the implantable lead may connect to an IMD including a therapy module configured to generate one or more electrical stimulation signals. As part of the cardiac therapy, electrical stimulation signals, such as, e.g., pacing, cardioversion and/or defibrillation signals, generated by a therapy module of an IMD may be delivered to the heart of the patient via one or more electrodes arranged on a distal portion of the implantable lead. To deliver the electrical stimulation generated by the therapy module of the IMD to the heart of the patient, the one or more implantable leads can be positioned within the patient such that one or more of the lead electrodes on the distal portion of the lead are adjacent to the target cardiac tissue site while the proximal end of the lead is coupled to the IMD.

The one or more lead electrodes on the distal portion of the lead body may be distributed axially along the lead body. In some examples, an implantable lead may include an insulating member, such as, e.g., as insulating sleeve, that surrounds a distal portion of the lead body proximate to one or more of the lead electrodes. The insulating member defines one or more apertures sized to allow at least a portion of the one or more electrodes to be partially exposed to a target tissue site when the insulating member occupies certain positions on the lead body. By moving the insulating member axially and/or radially over the lead body, electrodes may be selectively exposed and covered from the tissue adjacent the electrode surface based on the position of the insulating member relative the lead body.

Such a relationship may be utilized by a clinician during adjust the electrical stimulation delivered be the lead to a patient. For example, once an implantable lead is positioned within the heart of a patient, a clinician may move the insulating sleeve over the lead body until the orientation of the insulating member relative the distal portion of the lead body produces the desired electrical stimulation to the heart of the patient. A clinician may move the insulating sleeve in the radial direction and/or axial direction to direct the electrical stimulation field delivered by the lead electrode(s) to the cardiac tissue of the patient.

Depending the location of the implantable lead within a patient, a clinician may only have limited access to the distal portion of the lead body on which the one or more electrodes are arranged, and the ability of the clinician to move the insulating member in the axially and/or radial direction over the distal portion of the lead as described may be limited. For example, when an implantable lead is positioned within the heart of a patient, e.g., within the left ventricle, a clinician may not have direct access to the distal portion of the lead. Rather, the clinician may control the position of the distal portion of the lead by moving the proximal portion of the lead, which may be more easily accessed by the clinician based on the location of the IMD within the patient.

Similarly, the ability of the clinician to move an insulting member in a radial and/or axial direction over the distal portion of the lead body when the distal portion of the lead is positioned within the heart of a patient is limited. In some examples, an insulating member may be configured to extend axially over a substantial portion the lead body to allow a clinician to access the insulating member over a proximal portion of the lead body. However, the composition and structure of the insulating member may prevent or inhibit the remote movement of the distal portion of the insulating member through movement of the proximal portion, at least to the extent that relatively precise control over the proximal end of the insulating member is required. For example, the ability of insulating sleeve to transfer torque from the proximal to distal portion when rotational force is applied to the sleeve at the proximal portion of the lead body may be insufficient to actuate the distal portion of the insulating sleeve of the distal portion of the lead body with the precision required to selectively expose and cover electrodes on the distal end of the lead. In some cases, the insulating member may store the rotational force over the length of the insulating member causing the insulating sleeve to periodically and undesirably rotate after the distal portion of the insulating sleeve has been desirably positioned radially relative to one or more electrode on the lead.

Moreover, if an implantable lead is initially positioned within a patient without the insulating member positioned over the distal portion of the lead body, a clinician may be required to slide the insulating member over the lead body from the proximal end of the lead to the distal portion while the implantable lead is positioned within the heart. Again, the composition and structure of the insulating member may prevent or inhibit a clinician from sliding the proximal portion of the insulating member from a proximal portion to a distal portion of the lead body, especially in situations in which the lead body follows a relatively tortuous path, e.g., as with an left ventricle lead.

As will be described in further detail below, an implantable lead may further include reinforcement member that is coupled to the insulating member. The reinforcement member may be configured to couple to the insulating member at or near the distal portion of a lead body and extend to the proximal portion of the lead body. The reinforcement member may be formed at least in part (e.g., partially or substantially entirely) of a different material than that of the insulating member. The composition and structure of the reinforcement member provides suitable transfer of rotational force applied the reinforcement member over the proximal portion of the lead body to the insulating member positioned over the distal portion of the lead body. For example, the reinforcement member may be formed with a wire braid structure configured to provide adequate transfer of radially force to position the insulating member in the radial direction over the distal portion of the lead body from the proximal portion of the lead. Additionally, the composition and structure of the reinforcement member may increase the transfer of axial force applied to the reinforcement member over the proximal portion of the lead body to the insulating member positioned over the distal portion of the lead body.

In some example, the reinforcement member may be configured to protect the lead against one or more undesirable side-effects from magnetic resonance imaging (MRI). For example, the reinforcement member may be formed of an electrically conductive material to shields conductors within a lead body from electromagnetic fields and/or radio frequency fields associated with an MRI scan. Additionally, the reinforcement member may protect the lead body against crush.

The systems and devices described in the disclosure may include at least one insulating member configured to surround at least a portion of an implantable lead body and a reinforcement member coupled to the insulating member. While examples of the present disclosure are described with regard to electrical stimulation therapy systems configured to deliver cardiac rhythm management therapy, e.g., pacing, cardioversion, and/or defibrillation signals, to the heart of a patient, examples are not limited to such an application. Examples of the disclosure may also be applicable to implantable leads used for delivering neurostimulation therapy to one or more tissue sites of a patient, such as the vagal nerve stimulation or spinal cord stimulation. In some cases, examples of the present disclosure may include implantable leads used to deliver deep brain stimulation to a patient, or implantable leads configured to deliver electrical stimulation therapy to a patient to treat urinary incontinence, e.g., by directionally stimulating one or more nerve sites and not the surround muscle.

FIG. 1 is a conceptual diagram illustrating an example therapy system 10 that may be used to provide therapy to patient 12. Patient 12 ordinarily, but not necessarily, will be a human. Therapy system 10 includes implantable medical device (IMD) 14, lead 16, and programmer 28.

IMD 14 may generate and deliver electrical stimulation to heart 18 via electrodes (not shown) carried by lead 16 in order to manage a cardiac rhythm of heart 18. Accordingly, IMD 14 may include a therapy module (not shown) configured to generate at least one of pacing, cardioversion, or defibrillation therapy. The pacing therapy may include, for example, anti-tachyarrhythmia pacing (ATP) and pacing therapies designed to prevent ventricular tachycardia, ventricular fibrillation, atrial tachycardia, and/or atrial fibrillation. In some examples, IMD 14 may deliver pacing pulses, but not cardioversion or defibrillation pulses, while in other examples, IMD 14 may deliver cardioversion or defibrillation pulses, but not pacing pulses. In addition, in further examples, IMD 14 may deliver pacing, cardioversion, and defibrillation pulses.

In the example shown in FIG. 1, lead 16 extends through one or more veins (not shown), the superior vena cava (not shown), and right atrium 22, and into right ventricle 20. Although not shown in FIG. 1, therapy system 10 may additionally or alternatively include a left ventricular (LV) coronary sinus lead that extends through one or more veins, the vena cava, right atrium 22, and into the coronary sinus to a region adjacent to the free wall of left ventricle 26 of heart 18. Therapy system may also additionally or alternatively include an atrial (RA) lead that extends through one or more veins and the vena cava, and into the right atrium 22 of heart 18. In other examples, IMD 14 may deliver stimulation therapy to heart 18 by delivering stimulation to an extravascular tissue site in addition to or instead of delivering stimulation via electrodes of intravascular lead 16. An extravascular tissue site may be outside of heart 18 and outside of arteries, veins, or other vasculature of patient 12. In some examples, lead 16 may be positioned epicardially to deliver electrically stimulation to heart 18 of patient 12.

IMD 14 may sense electrical signals attendant to the depolarization and repolarization of heart 18 via electrodes (not shown) coupled to lead 16. In some examples, IMD 14 may provide pacing pulses to heart 18 based on the electrical signals sensed within heart 18. The configurations of electrodes used by IMD 14 for sensing and pacing may be unipolar or bipolar. IMD 14 may also provide defibrillation therapy and/or cardioversion therapy via electrodes located on lead 16. IMD 14 may detect arrhythmia of heart 18, such as fibrillation of ventricles 20 and 26, and IMD 14 may be programmed to deliver a progression of therapies, e.g., pulses with increasing energy levels, until a fibrillation of heart 18 is stopped. IMD 14 may detect fibrillation employing one or more fibrillation detection techniques known in the art.

In some examples, IMD 14 may also be referred to as a signal generator, stimulation generator or an electrical stimulator. In some examples, lead 16 may also carry one or more sense electrodes to permit IMD 14 to sense electrical signals within patient 12. In the example of FIG. 1, IMD 14 has been implanted in patient 12 at a location that allows leads 16 to be positioned within heart 26. For example, IMD 14 may be subcutaneously or submuscularly implanted in the body of a patient 12 (e.g., in a chest cavity, lower back, lower abdomen, or buttocks of patient 12). The components for generating and delivering the pacing, cardioversion and/or defibrillation therapy via leads 16 may be substantially contained within housing 30 of IMD 14. Proximal end 16A of lead 16 is mechanically and electrically coupled to IMD 14 via lead connection header 32 either directly or indirectly (e.g., via a lead extension). In particular, conductors disposed in the lead body of lead 28 may electrically connect stimulation electrodes (and sense electrodes, if present) of lead 28 to IMD 14.

In some examples, IMD 14 may include one or more housing electrodes, which may be formed integrally with an outer surface of hermetically-sealed housing 28 of IMD 14 or otherwise coupled to housing 28. In some examples, the housing electrode may be defined by an uninsulated portion of an outward facing portion of housing 28. Other divisions between insulated and uninsulated portions of housing 30 may be employed to define two or more housing electrodes. In some examples, such as the example shown in FIG. 1, the housing electrode may comprise substantially all of housing 30. In other examples, one or more electrodes may be embedded into an insulating casing that surrounds the outer surface of housing 30. Any of the electrodes of lead 16 may be used for unipolar sensing or stimulation in combination with the housing electrode.

As shown in FIG. 1, therapy system 10 also includes programmer 28. In some examples, programmer 28 may be a handheld computing device or a computer workstation. Programmer 28 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 28 can additionally or alternatively include a peripheral pointing device, such as a mouse, via which a user may interact with the user interface. In some examples, a display of programmer 28 may include a touch screen display, and a user may interact with programmer 28 via the display.

A user, such as a physician, technician, or other clinician, may interact with programmer 28 to communicate with IMD 14. For example, the user may interact with programmer 28 to retrieve physiological or diagnostic information from IMD 14. A user may also interact with programmer 28 to program IMD 14, e.g., select values for operational parameters for one or more of the stimulation therapies delivered by IMD 14. For example, the user may use programmer 28 to retrieve information from IMD 14 regarding the rhythm of heart 18, trends therein over time, or tachyarrhythmia episodes. As another example, the user may use programmer 28 to retrieve information from IMD 14 regarding other sensed physiological parameters of patient 12, such as electrical depolarization/repolarization signals from heart 18 (referred to as "electrogram" or EGM), intracardiac or intravascular pressure, activity, posture, respiration, or thoracic impedance. As another example, the user may use programmer 28 to retrieve information from IMD 14 regarding the performance or integrity of IMD 14 or other components of system 10 corresponding to the first stimulation therapy, such as lead 16, or a power source of IMD 14.

Programmer 28 may communicate with IMD 14 via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 14 implant site in order to improve the quality or security of communication between IMD 14 and programmer 28.

As shown in FIG. 1, lead 16 includes reinforcement member 34 and insulating member 36. Insulating member 36 surrounds the body of lead 16 over distal portion 16B positioned within right ventricle 20, which includes one or more electrodes (not shown). Reinforcement member 34 is coupled to insulating member 36 and extends axially over the body of lead 16 from the insulating member 36 to a proximal portion of lead 16 located outside heart 18. Insulating member 36 defines one or more apertures (not shown) that may expose at least a portion of one or more electrodes (not shown) on lead 16 to cardiac tissue of heart 18 when in a first position on the body of lead 16. When the proximal portion of reinforcement member 34 is moved in either the axial and/or radial direction over the body of lead 16, the force applied to reinforcement member 34 is transferred to insulating member 36 thereby moving insulating member 36 over the body of lead 16 in the same manner.

FIGS. 2A-2C are conceptual diagrams illustrating example lead 38 including reinforcement member 34 and insulating member 36. Reinforcement member 34 and insulating member 36 extend axially over lead body 40. Lead 38 may be an implantable lead configured to delivery electrical stimulation therapy to patient 12 from an IMD 14 (FIG. 1). In some examples, lead 38 may deliver cardiac rhythm management therapy to patient 12, and may be substantially the same or similar to lead 16 (FIG. 1).

Lead 16 has an elongated lead body 40 including distal portion 40B and proximal portion 40A. The end of proximal portion 40A of lead 16 may be configured to connect to connection header 32 of IMD 14 (FIG. 1) to electrically and mechanically couple lead 16 to the therapy module (not shown) of IMD 14. Distal portion 40B of lead body may be configured to be positioned with heart 18 of patient 12 to deliver electrical stimulation signals to tissue of heart 18 adjacent to electrodes 46, 48, and/or 50. Lead body 40 may be formed of a biocompatible material such as, e.g., polyurethane. Lead body 40 may have a substantially tubular form and may define a substantially circular cross-section. Alternative shapes of lead body 40 are contemplated, e.g., lead body 40 may have an oval or square cross-section.

Electrodes 46, 48, 50 are arranged on distal portion 40B of lead body 40. Electrodes 46 and 48 may form a substantially cylindrical ring of conductive material extending radially around a portion of lead body 40 and, in some cases, may be referred to as ring electrodes. Electrode 50 includes a conductive material formed on the distal end of lead body 40 and, in some cases, may be referred to as a tip electrode. Electrodes 46, 48, and 50 may each be used to deliver electrical stimulation signals, such as cardiac pacing signals, generated by the therapy module of IMD 14 to heart 18 of patient 12 (FIG. 1). For example, when lead 38 is properly connected to IMD 14, electrical stimulation signals generated by the therapy module of IMD 14 may be conducted via one or more conductors provided within lead body 40 to one or more of electrodes 46, 48, 50, which may deliver the electrical stimulation signals to heart 18 of patient 12. Lead 38 may include any suitable number of electrodes. For examples, lead 38 may include one, two, three, four, five or more than five electrodes.

Insulating member 36 extends axially over a distal portion 40B of lead body 40, and defines aperture 42A and aperture 42B (collectively "apertures 42"). As shown, insulating member 36 may have a tubular shape or body which surrounds the outer surface of a distal portion of lead body 40. In some examples, insulating member may be referred in some cases as a tubular insulating sleeve. Insulating member 36 is sized such that the inner lumen defined by the inner surface of insulating member 36 receives the distal portion 40B of lead body 40. Insulating member 36 may be separate from lead body 40 to allow insulating member 36 may be moved axially and/or radially relative lead body 40 when insulating member 36 and reinforcement member 34 is not anchored relative to lead body 40.

Apertures 42 are sized and shaped to expose portions of electrodes 46 and 48 carried by lead 38 to facilitate the selection of electrodes 46 and 48, and directional application of stimulation via the one or more selected electrode 46 and 48. By moving insulating member 36 over the body of lead 16 in the axial and/or radial direction via reinforcement member 34, the relationship of apertures 42 relative to electrodes 46 and 48 may be adjusted to selectively expose and/or cover portions of electrodes 46 and 48. In general, the portions of electrode 46 and 48 covered by insulating member 36 will be electrically insulated, and the portions of electrodes 46 and 48 exposed by apertures 42 will be capable of conducting electrical stimulation to the adjacent tissue within heart 18. Insulating member 36 may define any suitable number of apertures having any suitable size and configuration. For example, insulating member 36 may define one or a plurality of apertures, e.g., two, three, four or more than four apertures. In some examples, insulating member 36 may include the same number of apertures as electrodes carried by lead 38, while in others insulating member 36 may have more or less apertures than the number of electrode carried by lead 38.

Insulating member 36 may be formed of any suitable material including biocompatible plastics and other insulating materials that allow insulating member 36 to electrically insulate electrodes 46 and 48, as described herein. For example, insulating member 36 may be formed from polyurethane, pellethane, copolymer made from urethane and silicone blend, or the like. In one example, insulating member 36 may include DOW 2363-55D polyurethane. Apertures 42 may be cut from or machined within a length of tubing to form insulating member 36. Alternatively, insulating member 36 can be formed by injection molding, vulcanization molding, or any other suitable know technique. In any case, insulating member 36 is configured to be positioned over distal portion 40B of lead body 40 that includes one or more electrode, such as electrodes 46 and 48. Insulating member 36 has a wall thickness that is sufficiently thin to allow for implantation within heart 18 of patient (or whichever portion of patient 12 that lead 38 is configured to be implanted), but also sufficiently thick to retain electrically insulative properties and avoid electrical breakdown when in contact with a covered portion of electrode 46 and/or electrode 48.

Reinforcement member 34 is coupled to insulating member 36 positioned on distal end 40B of lead body 40. As shown, reinforcement member 34 may have a tubular shape which surrounds lead body 40 and extends axially over lead body 40 from distal portion 40B to proximal portion 40A. Reinforcement member 34 is sized to define an inner lumen that receives lead body 40. Reinforcement member 34 may be separate from lead body 40 to allow reinforcement member 34 may be moved axially and/or radially relative lead body 40 when insulating member 36 and/or reinforcement member is not anchored relative to lead body 40.

As previously described, reinforcement member 34 be configured to transfer rotational and/or axial force applied to reinforcement member 34 at a location proximate the proximal portion 40A of lead body 30 to insulating member 36 positioned over the distal portion 40B of lead body 30. In this manner, an axial and/or rotational force may be applied to reinforcement member 34 relative the distal portion 40A of lead body 40 to move insulating member 36 over the distal portion 40B of lead body 40. By moving insulating member 36 via reinforcement member 34, select portions of electrodes 46 and 48 may be exposed by apertures 42 to conduct electrical stimulation to tissue, e.g., cardiac tissue, adjacent the exposed electrode portion. Such a technique may be utilized by a clinician to adjust the position of insulating member 36 relative lead body 40 when distal portion 40B is implanted within heart 18, or other implant site, of patient 12 and not directly accessible to the clinician. In some cases, lead body 40 may follow a relatively tortuous path from the proximal portion 40A to the distal portion 40B (e.g., when distal portion 40B of lead body 40 is positioned within the left ventricle 26 of heart 18). As such, reinforcement member 40 facilitates the transfer of force from a location near the proximal portion 40A of lead body 40 to insulating member 36 positioned over distal portion 40B of lead body 40.

As shown, FIGS. 2A-2C illustrate the movement of reinforcement member 34 and insulating member 36 over lead body 40, e.g., based on the application of an axial force to the proximal portion of reinforcement member 34. Progressing in order from FIG. 2A to 2B to 2C, an axial force is applied toward the proximal end of lead 38, e.g., by a clinician, to a location on reinforcement member 34 near the proximal portion of lead body 40. Reinforcement member 34 transfers the axial force to insulating member 36 positioned on the distal portion 40B of lead body 40, which actuates insulating member 36 over the outer surface of lead body 40 in the proximal direction. In FIG. 2A, a portion of electrode 46 is exposed by aperture 42A of insulating member 36 and electrode 48 is entirely covered by insulating member 36. However, the movement of insulating member 36 in the proximal direction via reinforcement member 34 changes the orientation of insulating member 36 relative to lead body 40 and electrode 46 and 48. In FIG. 2B, a portion of both electrodes 46 and 48 are exposed by aperture 42A and 42B, respectfully, by moving insulating member a distance of $L_1$ in the proximal direction over lead body 40. From that point, insulating member 36 may be moved a distance of $L_2$ in the proximal direction over lead body 40 to exposed a portion of electrode 48 via aperture 42B and cover electrode 46. In this manner, reinforcement member 34 may transfer an applied axial force to move insulating member 36 over distal portion 40B of lead body 40 to selectively expose and cover portions of electrodes 46 and 48. In some examples, such a technique may be used to essentially vary the tip to ring spacing on a pacing lead.

Although not directly illustrated in FIGS. 2A-2C, insulating member 36 may be moved in the radial direction over lead body 40 by applying a force to reinforcement member 34 in the radial direction to the proximal portion of reinforcement member 34. Reinforcement member 34 transfers the radial force to insulating member 36, which rotates insulating member 36 over lead body 40 along with reinforcement member 34. In this manner, insulating sleeve 36 may be rotated over distal portion 40B of lead body 40 via application of a force in the radial direction to a proximal portion of reinforcement member 34 to selectively expose and cover portions of electrodes 46 and 48 via apertures 42. Such a technique may facilitate to the directional delivery of electrical stimulation to a target tissue by providing for control of the stimulation in the radial direction. In cardiac applications, the directional delivery of electrical stimulation via electrodes 46 and/or 48 may be utilized to avoid phrenic nerve stimulation.

Reinforcement member 34 may be formed of any suitable material and structure that provide one or more of the properties attributed to reinforcement member 34 herein. Reinforcement member 34 may be formed of a material that is different than that of the material of insulating member 36. In some examples, reinforcement member 34 may include a braided structure that provides suitable transfer of rotational and/or axial force. The braided structure may include a plurality of metal or metal alloy wires braided with one another to form a braided metallic sleeve configured fit of over lead body 40. The wires may be formed from any suitable metal and/or metal alloys, such as, e.g., titanium, stainless steel, tantalum, and the like. The diameter of individual wire strands in a braided structure may range from approximately 0.5 mils to approximately 2.5 mils, such as, e.g., approximately 0.5 mils to approximately 1.5 mils, approximately 1 mil to approximately 2.5 mils, or approximately 1.2 mils to approximately 1.7 mils. In some examples, the braided wire may be formed of cobalt chromium alloys, such as, e.g., MP35N or Elgiloy (Phynox), stainless steel, e.g., 316L VAR, or nickel-titanium alloy (Nitinol). In one example, the braided wire may be formed of a titanium alloy wire, such as, e.g., Ti 6Al 4V ELI, having a diameter of approximately 1.5 mils annealed.

The reinforcement member may be braided in any suitable pattern. For example, the braided structure may have approximately 60 to approximately 120 picks per inch, such as approximately 90 to approximately 100 picks per inch. The braided structure may include 12 to 48 wire strands. In one example, a 16 tow pattern, with two wires per tow, may be braided in a two over one pattern to form the braided wire structure of reinforcement member 34.

The braided wire may form a braided wire sleeve defining an inner lumen that receives lead body 40. In some examples, the void spaces of the braided structure may be filled in with one or more suitable biocompatible polymeric materials, such as, e.g., polyurethane. For example, the braided wire structure may be embedded within the walls of the polymer structure to form reinforcement member 34. In this manner, a reinforcement member formed of a braided structure may define a continuous surface over lead body 40. In some examples, such polymeric structure of reinforcement member 34 may be substantially the same insulating material used to form insulating member 36. The braided structure may be embedded in the insulating material to provide suitable transfer of radial and/or axial force applied to the proximal portion of reinforcement member 34 over lead body 40 to insulating member 36 positioned over distal portion 40B of lead body 40. Additionally or alternatively, the braided structure may be bonded to the inner or outer surface of a polymeric tube. In other examples, individual strands, e.g., metallic wire strands, may be coated with a polymer material and then braided with one another to form reinforcement member 40.

The braid pattern and braid material may be selected to provide desired properties of reinforcement member 34. In addition, the percentage and location of the braided structure over the overall length of reinforcement member 34 may be varied to provide desirable properties. In some examples, substantially the entire length of reinforcement member 34 includes a braided structure. Alternatively, only certain portions of the overall length of reinforcement member may include a braided structure. For example, reinforcement member 34 may include a braided structure over approximately 25 to approximately 97 percent of the overall length of reinforcement member 34, such as, e.g., approximately 85 to approximately 95 percent, approximately 25 to approximately 75 percent, or approximately 50 to approximately 97 percent of the overall length of reinforcement member 34. The remaining portions of reinforcement member 34 may be formed primary of polymeric material, e.g., a tube shaped polymer structure, without the incorporation of a braided structure. Reinforcement member 34 may include a braided structure in those portions that correspond to particularly tortuous areas along the implant path of lead 38 within patient 12 to increase the transfer of radial and/or axial force in reinforcement member 34 over such portions.

The inner surface of reinforcement member 34 that defines the inner lumen which receives lead body 40 may include a lubricant that promotes the movement of reinforcement member 34 over lead body 40 when an axial and/or radial force is applied. The lubricating material may reduce frictional interaction between reinforcement member 34 and the outer surface of lead body 40 to prevent abrasion and/or fracture of either reinforcement member 34 or lead body 40. In some examples, the inner surface of reinforcement member 34 may include a lubricating layer at the interface between the outer surface of lead body 40 and reinforcement member 34 when reinforcement member 34 surrounds lead body 40.

Any suitable lubricating material may be used for reinforcement member 34. For example, silicone oil, saline, PTFE coating insulation, polyacrylamide hydrophilic, Dow Corning MDX4-4159 Medical Grade Dispersion, and the like may be used for lubrication between the reinforcement member 34 and lead body 40. In some examples, a material that fills the void space of a braided structure, as described above, may be a lubricating material. In such a configuration, the material may separate the braided structure from the outer surface of the lead body, which prevents the braided structure from making direct contact with the outer surface of the lead body. Depending the material and pattern of the braided structure, such direct interaction between the braided structure and lead body can result in abrasive contact or fracture of the lead body. In some examples, the inner surface of reinforcement member 34 may undergo siloxane surface treatment to lubricate the interaction between reinforcement member 34 and lead body 40.

In some examples, the outer surface of lead body 40 may include one or more sealing protrusions extending around the circumference of lead body 40 between electrode 46 and 48. The protrusion on the outer surface may be configured to electrically isolate electrodes 46 and 48 from one another by providing a fluid seal between the electrodes.

Reinforcement member 34 may be configured to provide shielding to lead 38 from external alternating electromagnetic fields, e.g., such as those produced during MRI scans. As identified above, implantable leads of an IMD can be adversely affected when a patient is exposed to alternating electromagnetic fields. For example, without such shielding, alternating electromagnetic fields produced during an MRI may induce undesired currents within lead 38, which can discharge via electrodes 46, 48, and/or 50 to the adjacent tissue to patient 12. To electrically shield all or a portion of lead 38, reinforcement member 34 may include suitable electrically conductive material(s) to electrically shield the one or more conductors within lead body 40 that electrically couple electrodes 46, 48, 50 to the therapy module within IMD 14.

In some examples, reinforcement member 34 may include metal and metal alloy wires that exhibit relatively high electrical conductivity. For example, wire including gold, platinum, palladium, silver, tantalum, tantalum-tungsten-niobium alloy, and the like may be used to form a braided structure for reinforcement member 34. Additionally or alternatively, reinforcement member 34 may include a non-metallic material that exhibits relatively high electrical conductivity. For example, the non-metallic conductive material may include carbon (e.g., in the form of graphite, continuous carbon fiber strands and/or polymer strands impregnated with carbon nanotubes) to provide a high conductivity reinforcement member that electrically shield lead 38 from electromagnetic and/or RF energy. Other highly conductive, non-metallic materials may also be used for reinforcement member 34.

Reinforcement member 34 may have any suitable length. The length of reinforcement member 34 may depend on the position of electrode 46 and 48 on lead 38, the implant location of lead 38 within patient 12, and/or the length of insulating member 36. In general, it is desirable for reinforcement member 34 to have length that allows a clinician to directly access at least the proximal portion of reinforcement member 34, e.g., at the implant site of IMD 14 within patient 12, when apertures 42 of insulating member 36 are proximate to electrodes 46 and 48, so that the clinician may directly apply an axial and/or radial force to reinforcement member 34 to move insulating sleeve 36 over distal portion 40 B of lead body 40 even though insulating sleeve is positioned within patient 12 at a location that is not directly accessible to the clinician.

As shown in FIG. 1, the length of reinforcement member 34 is such that reinforcement member 34 extends from insulating member 36 positioned over the distal portion 16B of lead 16 within right ventricle 20 of heart 18 to a point adjacent the proximal end 16A of lead 16 that connects to header 32 of IMD 14. In other examples, reinforcement member 34 may have a length that does not extend to the proximal end 16A of lead 16, but still has a length that allows a clinician to directly access a portion of reinforcement member 34 when insulating member 36 and lead 16 are desirable positioned within patient 12.

In some examples, reinforcement member 34 may extend substantially the entire length of lead 16 from the distal end to the proximal end, e.g., in examples in which reinforcement member 34 shields lead from electromagnetic and/or RF fields of MRI scans. In such an example, reinforcement member 34 may extend along substantially the entire length from proximal end 16A of lead 16 (FIG. 1) which connects to the header 32 of IMD 14 (FIG. 1) to insulating member 36. In some examples, reinforcement member 34 may extend substantially the entire length of lead 16 to shield substantially all of lead 16 from electromagnetic and/or RF fields. In such cases, since insulating member 36 may or may not be positioned directly adjacent to the distal end of lead 16, reinforcement member 34 may extend over lead body 40 beyond insulating member 36 to the distal end of lead 16 to shield substantially the entire portion of lead body 40. In some examples, reinforcement member 34 may extend approximately 10 to approximately 80 percent of the overall length of lead 38, such as, e.g., approximately 25 to approximately 80 percent of the overall length of lead 38.

Reinforcement member 34 may be coupled to insulating member 36 is any suitable manner that allows reinforcement member 34 to transfer a force applied to a portion of reinforcement member, e.g., a proximal portion, in the radial and/or axial direction to insulating member 36, as described herein. In some examples, the coupling of reinforcement member 34 to insulating sleeve 36 allows insulating member 36 to be positioned radially and axially over lead body 40 even when insulating member 36 at a location within patient 12, e.g., heart 18, which is not directly accessible by a clinician. In this manner, reinforcement member 34 may facilitate the movement of insulating member 36 over lead body 40 to selectively expose and cover portions of electrodes 46 and 48.

FIG. 3 is a conceptual diagram illustrating a distal portion of lead 62 including reinforcement member 66 and insulating member 68. Lead 62, reinforcement member 66 and insulating member 58 may be the same or substantially similar to that of lead 38, reinforcement member 34 and insulating member 36, respectively. Lead 62 may include one or more electrode (not shown) on lead body 64. Insulating member 68 may be moved over the outer surface of lead body 64 by applying a force in the axial and/or radial direction to reinforcement member 66 to selectively expose portions of the one or more electrodes of lead 62 via aperture 72.

As shown, reinforcement member 66 includes a braided structure bonded to the outer surface of a polymer sleeve that surrounds lead body 64. The distal end of reinforcement member (66) is directly coupled to the proximal end of insulating member 68. Within area 70, the braided structure, e.g., braided metallic wire structure, of reinforcement member 66 terminates moving distally over lead body 64, and insulating member 68 extends distally over lead body 64 without braided structure. For examples in which insulating member 68 is formed of a different material composition than the material in which the braided structure of reinforcement member 66 is bonded, one or more suitable methods may be used to bond such materials to one another. In examples in which the insulating member 68 is formed of substantially the same material as the material in which the braided structure of reinforcement member 66 is bonded, reinforcement member 66 and insulating member 68 may be formed of a single piece of tubular material, and the braided structure may be bonded to the tubular material to define reinforcement member 68.

FIG. 4 is a conceptual is a conceptual diagram illustrating a distal portion of lead 74 including reinforcement member 76 and insulating member 78. Reinforcement member 76 and insulating member 78 extend axially over lead body 64, and insulating member 78 define aperture 80 to selectively expose portions of one or more electrodes (not shown) carried on lead body 64, as described herein.

Lead 74, reinforcement member 76 and insulating member 78 may be the same or substantially similar to that of lead 62, reinforcement member 66 and insulating member 68. However, the braided structure of reinforcement member 76 extends into insulating member 68, and terminates along the boundary of insulating member 78 that defines aperture 80 and also at the distal end of insulating member 78. In this manner, if configured to electrically shield the one or more conductors within lead body 82, the braided structure may provide such shielding over the portion of lead body 82 covered by insulating member 78 in addition to the portion of lead body 82 covered by reinforcement member 76.

The braided structure may be terminated using any suitable technique to prevent shorting and/or individual braid wires from extending out of the material at the location that the braided structure is terminated. In some examples, a termination ring that extends around a portion of the reinforcement member and/or insulating member may cover the termination of the braided wire structure. For example, a metallic termination ring (e.g., a titanium ring) may be used to cover the termination of the braided structure within area 70 (FIG. 3) or at the distal end of insulating member 78 (FIG. 4) to cover termination of the braided structure in such an example. The metallic termination ring may be located on the inner and/or outer surface of the reinforcement member/insulating member to correspond to the position of the braided structure. Alternatively or additionally, a polymer ring (e.g., a polyurethane ring) may cover the termination of the braided structure in a similar fashion. Such a polymer material may also frame aperture 80 (FIG. 4) to cover the termination of the braided structure terminating adjacent to the boundary of aperture 80 (FIG. 4). The polymer material which covers the termination of the braided structure may be the same different from that of the polymer material of the insulating member.

FIGS. 5A and 5B are conceptual diagrams illustrating example lead 52 including reinforcement member 34 and insulating member 36. Lead 52 may be the same or substantially similar to that of lead 38 of FIGS. 2A and 2B. However, lead 52 includes electrodes 54, 56, 58, 60 rather than electrodes 46, 48, 50. The conductive surfaces of electrodes 54, 56, 58, 60 extend around approximately half, i.e., approximately 180 degrees around, of lead body 40 in the radial direction. Electrodes 54 and 56 each extend around approximately the same half of lead body 40 and electrodes 58 and 60 each extend around approximately the same half of lead body.

Similar to lead 38 (FIGS. 2A-2C), reinforcement member 34 and insulating member 36 extend axially over lead body 40. Insulating member 36 is positioned over lead body 40 such that apertures 42A and 42B are proximate to electrodes 54, 56, 58, 60. In FIG. 5A, a portion of electrode 54 is exposed via aperture 42A of insulating member 36 and a portion of electrode 56 is exposed via aperture 42B of insulating member 36. In FIG. 5B, lead body 40 is rotated in the radial direction approximately 180 degrees within the inner lumen defined by reinforcement member 34 and insulating member 36, e.g., by applying a force in the radial direction to proximal portion 40A of lead body 40. The rotation of lead body 40 relative to insulating member 36 results in electrode 54 and 56 being covered by insulating member 40 and portions of electrode 58 and 60 being exposed via apertures 42A and 42B, respectively. Of course, a similar result could be achieved by rotating insulating member 36 relative to distal portion 40B of lead body 40 by applying an appropriate radial force to reinforcement member 34 at proximal portion 40A of lead body 40. In such a case, reinforcement member 34 transfers the applied radial force to the insulating member 36 to move rotate the insulating member 36 over distal portion 40B of lead body 40 selectively expose and cover portions of electrodes 54, 56, 58, 60.

Electrode 54 and electrode 58 may have similar polarities (e.g., cathodic electrodes) and electrode 56 and electrode 60 may also have similar polarities but opposite of that of the polarity of electrodes 54 and 58 (e.g., anodic electrodes). Conductors within lead body 40 may electrically couple each electrode to the therapy module within IMD 14. In some examples, electrodes of similar polarities may be connected in series via conductors within lead body 40. For example, electrode 54 and electrode 58 may be connected in series electrode 56 and electrode 60 may be connected in series. In the manner, electrical stimulation may be conducted to electrodes 54, 56, 58, 60 via a single anodic conductive path and a single cathodic conductive path. The conductance of electrical stimulation to patient 12 is dictated by the portion of electrodes 54, 56, 58, 60 exposed to a tissue of patient 12 via apertures 42A and 42B.

In examples in which apertures 42 open towards a tissue target for stimulation, lead body 40 may be rotated within reinforcement member 34 and insulating member 36 to vary the axial position of the electrodes exposed to the target tissue (e.g., electrodes 54 and 56 versus electrodes 58 and 60). Alternatively, in example in which apertures 42 are not open toward a target tissue, lead body 40 may be held stationary and insulating member 36 may be rotated over distal portion 40B of lead body 40 via reinforcing member 34 to direct the stimulation field in the radial direction. In the example shown in FIGS. 5A and 5B, the rotation of insulating member 36 over lead body 40 may also change the axial position of the exposed electrodes (electrodes 54 and 56 versus electrodes 58 and 60). However, in examples in which lead 52 includes ring electrodes that entirely surround lead body 40 in the radial direction, rotating insulating member 36 over distal portion 40B of lead body 40 via reinforcing member 34 may direct the stimulation field in the radial direction without changing the axial position of the exposed electrodes.

Figure 6:
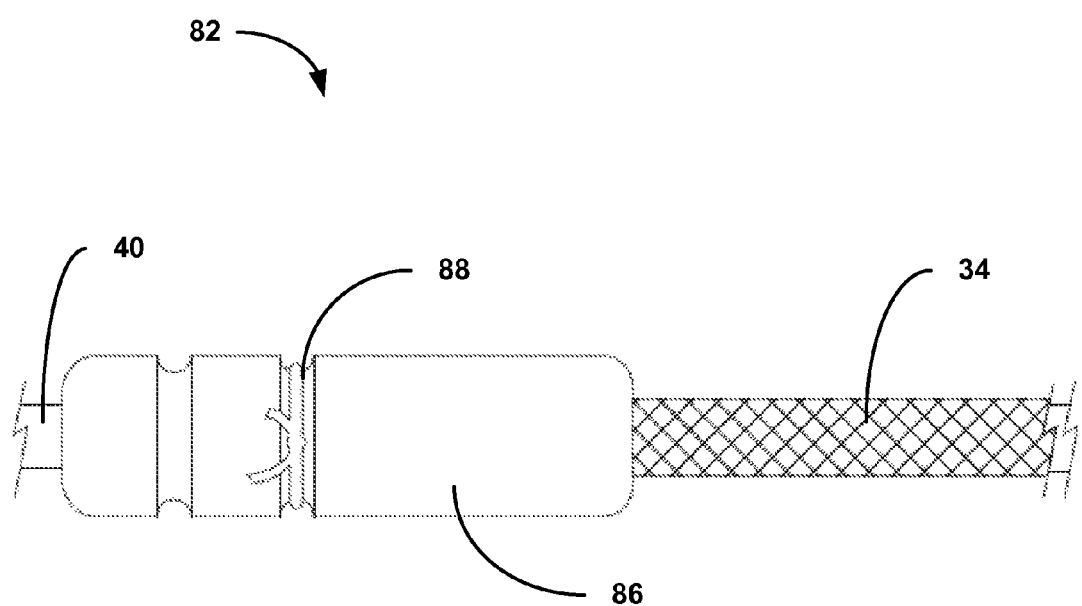
FIG. 6 is a conceptual diagram illustrating a proximal portion of an example lead.

FIG. 6 is a conceptual diagram illustrating a proximal portion of example lead 82. Lead 82 includes reinforcement member 38 and insulating member (not shown) that extend axially over lead body 40. In some aspects, lead 82 may be the same or substantially similar to that of lead 32 (FIGS. 2A-C). However, as shown in FIG. 6, lead anchor 86 is attached to the proximal end of reinforcement member 34, e.g., lead anchor 86 may be adhesively attached to reinforcement member 34 via liquid silicone rubber. Suture 88 may be tied to lead anchor 88 to frictionally engage lead body 40 to anchor the proximal end of reinforcement member 34 to lead body 40. When anchored to lead body 40 via lead anchor 86, the relative position of reinforcement member 34 and insulating member 36 (FIGS. 2A and 2B) relative to lead body 40 may be fixed in the axial and radial direction. In this manner, a clinician may fix the position of insulating member 36 over distal portion 40B (FIGS. 2A and 2B) of lead body 40 by anchoring the proximal end of reinforcement member 34 to lead body 40. Other suitable techniques may be used to anchor reinforcement member 34 to lead body 40 as described.

Figure 7A:
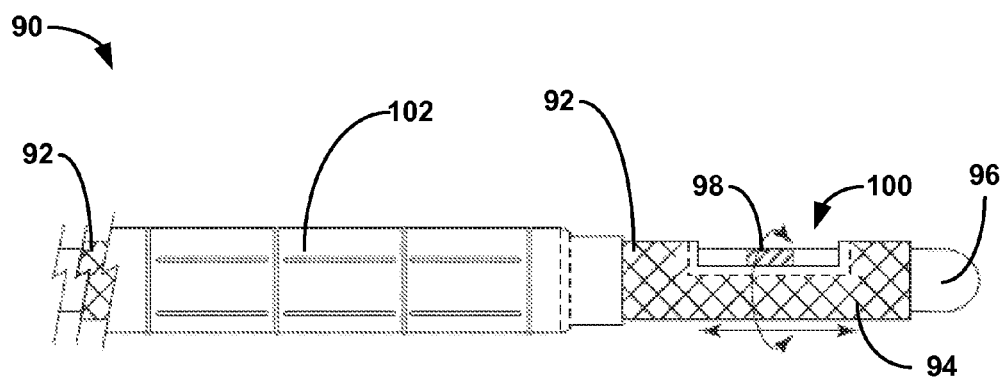
FIGS. 7A and 7B are conceptual diagrams illustrating a distal portion of an example lead.
Figure 7B:
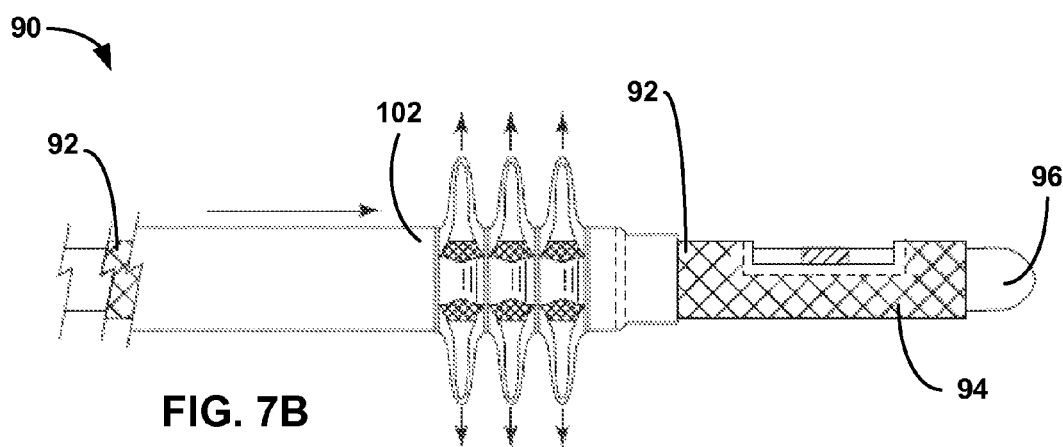

FIGS. 7A and 7B are conceptual diagrams illustrating a distal portion of example lead 90. Lead 90 includes reinforcement member 92 and insulating member 94 extending axially over lead body 96. Insulating member 94 define aperture 100, which is shown exposing a portion of electrode 98. In some aspects, lead 94 may be the same or similar to lead 74 (FIG. 4). However, lead 90 includes deployable lobe member 102 surrounding reinforcement member 92 adjacent to aperture 100 of insulating member 94. The distal end of deployable lobe member 102 may be affixed to the adjacent outer surface of reinforcement member 92. Deployable lobe member 102 may extend axially over the outer surfaces of reinforcement member 92 and lead body 96 to a proximal portion of reinforcement member 92, and may be used to stabilize and/or anchor reinforcement sleeve 92 and insulating member 94 within patient 12.

In the example of FIGS. 7A and 7B, deployable lobe member 102 includes a plurality of deployable lobes that protrude from and are circumferentially distributed about reinforcement member 92 and lead body 96. An example of deployable lobe member 102 may be the Attain® StarFix™ fixation element included in the over-the-wire lead Model 4195 developed and sold by Medtronic, Inc. of Minneapolis, Minn. The StarFix™ element generally includes a number of deployable lobes that are formed lengthwise on an insulating sheath that surrounds the medical lead by pairs of elongated, parallel cuts or slits. The deployable lobes are formed by the material between the elongated, substantially parallel slits. The spacing between the slits generally defines the width of the deployable lobe formed there between. Accordingly, the rigidity of each lobe may be increased or decreased by increasing or decreasing the distance between the parallel slits that define the lobe. The rigidity of the lobes may also be altered by using different types of materials and changing the thickness of the insulating sheath in which the slits are cut to produce the deployable lobes. The StarFix™ lobes are deployed by pushing the insulating sheath over reinforcement member 92. The pushing action causes the sleeve to become compressed, thus causing the extension of the deployable lobes outwardly.

The lobes of deployable lobe member 102 are shown in FIG. 7A in an undeployed state. As shown in FIG. 7B, by moving the proximal portion of deployable lobe member 102 over reinforcement member 92, the lobes of deployable lobe member deploy and extend outwardly to engage adjacent tissue of patient 12. In this manner, reinforcement member 92 and insulating member 94 may be stabilized and/or anchored within patient 12. Such a technique may be used once aperture 100 is desirable positioned adjacent tissue targeted for stimulation. In some examples, lead body 96 may be moved within insulating member 94 after insulating sleeve 94 has been anchored, e.g., to adjust the axial position of electrode 98. Lead body 96 may also be anchored within patient 12.

Once the lobes of deployable lobe member 102 have been deployed, the proximal end of the deployable lobe member may be fixed to reinforcement member 92, e.g., via an anchor similar to lead anchor 86 (FIG. 6) to maintain the lobes in the deployed position. The mechanism for anchoring reinforcement member 92 to lead body 96 may be separate from that of the mechanism for anchoring the proximal end of deployable lobe member 102 to reinforcement member 92 to allow lead body 40 to be moved within reinforcement member 92 while deployable lobe member 102, reinforcement member 92, and insulating member 94 are all fixed within patient 12. As necessary, the lobes of deployable lobe member 102 can be relaxed to allow for acute repositioning of reinforcement member by reducing compression on the lobe structure.

Examples of deployable lobe members for stabilizing and/or anchoring reinforcement member 92 and insulating member 94 within patient 12 include those described in U.S. Patent Publication No. 2004/0176782 A1, to George H. Hanse et al., filed Mar. 3, 2004, titled "METHOD AND APPARATUS FOR FIXATING AN IMPLANTABLE MEDICAL DEVICE," the entire content of which is incorporated herein by reference. However, other suitable techniques may be used to anchor reinforcement member 92 and insulating member 94 within patient 12.

In some examples, lead 90 may include both deployable lobe member 102 on the distal portion of reinforcement member 92 and lead anchor 86 (FIG. 6) on the proximal portion of reinforcement member 92. In such a configuration, insulating member 94 may be anchored within patient 12 via deployable lobe member 102, and reinforcement member 92 may be anchored to lead body 96 via lead anchor 86. In this manner, lead body 96, reinforcement member 92 and insulating member 94 may be fixed within patient 12 and fixed relative to one another.

Figure 8:
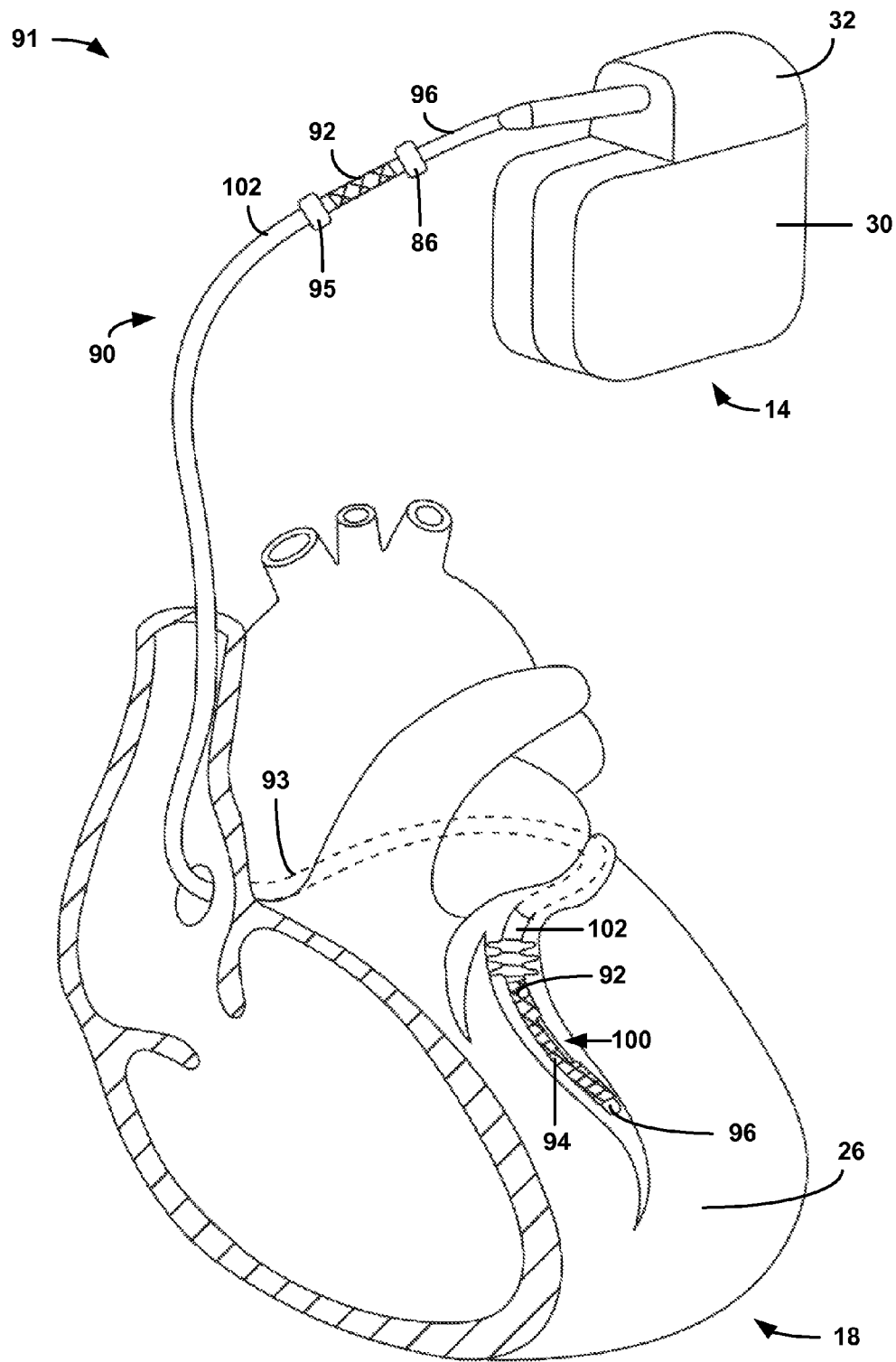
FIG. 8 is a conceptual diagram illustrating an example lead having a distal portion positioned within the heart of a patient.

FIG. 8 is a conceptual diagram illustrating an example therapy system 91 that may be used to provide therapy to patient 12. Therapy system 91 may be substantially the same or similar to that of therapy system 10. However, therapy system includes lead 90 connected to IMD 14 for delivery electrical stimulation to heart 18 of patient 12 (not shown) rather than lead 16 (FIG. 1). As described with regard to FIGS. 7A and 7B, lead 90 includes reinforcement member 92 and insulating member 94 extending axially over lead body 96. Insulating member 94 defines aperture 100, which may be used to selectively expose all or portions of one or more electrodes (not shown) located on the distal portion of lead body 96, as described herein.

As shown, a distal portion of lead 90 is positioned within heart 18 of patient 12. In particular, the distal portion of lead 90 is positioned proximate to the left ventricle 26 of patient 18 and, more particularly, within the coronary sinus 93 or a coronary vein accessed via the coronary sinus 93. In the illustrated embodiment, lead 90 is configured for intravenous introduction into heart 18. For example, lead 90 may have a lead body diameter of between 0.020 inches and 0.100 inches. Lead 90 may be referred to as a left ventricular (LV) lead.

Lead 90 also includes deployable lobe member 102 extending axially over lead body 96 and reinforcement member 92 to a proximal portion of reinforcement member 92. The distal end of deployable lobe member 102 is affixed to the outer surface of reinforcement member 92 adjacent insulating member 94. As shown in FIG. 8, the lobes on the distal portion of deployable lobe member 102 are deployed and extend outwardly to engage the adjacent tissue of the coronary vein of heart 18. In this manner, deployable lobe member 102 may be used to stabilize and/or anchor insulating member 94 and reinforcement member 92 within heart 18 of patient 12.

When a portion of lead 90 is positioned within the coronary sinus or a coronary vein as shown in FIG. 8, for example, one or more electrodes (not shown) on lead body 96 may be proximate to the phrenic nerve. Such positioning may result in unintentional phrenic nerve stimulation, which is generally undesirable during LV pacing therapy, depending on the stimulation field produced when an electrical stimulation signal is delivered to heart 18. For example, in some cases, phrenic nerve stimulation may cause a hiccup each time a stimulation signal is delivered to stimulate LV contraction, e.g., with each heart beat. As such, it may be desirable to selectively stimulate the myocardium of the left ventricle of heart 18 without stimulating the phrenic nerve.

The configuration of lead 90 may facilitate the direction of the electrical stimulation field generated by the delivery of electrical stimulation therapy to heart 18 via the electrode(s) on lead body 96 to prevent phrenic nerve stimulation. For example, to direct the electrical stimulation field to prevent phrenic nerve stimulation, once the distal portion of lead 90 has been positioned within coronary vein of heart 18 but before the lobes of deployable lobe member 102 are deployed, a clinician may move insulating member 94 axially and/or radially over lead body 96 via reinforcement member 92 to selectively expose all or portions of the electrode(s) on lead body 96 via aperture 100, as described herein. Additionally or alternatively, lead body 96 may also be moved within insulating member 94 to selectively expose all or portion of electrode(s) on lead body 96 via aperture 100. To evaluate a particular position of aperture 100 in insulating member 94 relative to the electrode(s) on lead body 96 and the tissue of heart 18, electrical stimulation may be delivered via the electrode(s) on leady body 96 to heart 18 of patient 12, and the physiological response of patient 12 associated with the resulting stimulation field may be monitored to determine whether or not phrenic nerve stimulation is present.

Such a process may be repeated until it is determined that insulating member 94 is in a desirable position relative the coronary vein and lead body 96, e.g., such that the stimulation field produced by the orientation results in adequate capture without phrenic nerve stimulation. At that time, the clinician may slide the proximal portion of deployable lobe member 102 over reinforcement member 92 and lead body 96 to deploy the lobes on the distal portion of deployable lobe member 102 to engage the tissue adjacent the lobe and anchor insulating member 94 and reinforcement member 92 at the desirable position within heart 18 of patient 12. Once the lobes are deployed, the proximal end of deployable lobe member 102 may be fixed relative to reinforcement member 92 via anchor member 95 to maintain the lobes of deployable lobe member 102 in the deployed state. In some examples, anchor member 95 may be substantially the same as anchor member 86 (FIG. 6).

As described above, the proximal end of reinforcement member 92 may be anchored relative to lead body 96 via anchor member 86 (FIG. 6). The combination of such fixation and the fixation of deployable lobe member 102 to reinforcement member 92, effectively fixes the position of deployable lobe member 102, reinforcement member 92 and insulating member 96 relative to one another and the adjacent tissue in heart 18. In some examples, prior to being fixed to reinforcement member 92 via anchor 96, lead body 96 may be moved within reinforcement member 92 and deployable lobe member 102 to further adjust the portion of electrode(s) exposed via aperture 100. Additionally or alternatively, after lead body 96 has been fixed to reinforcement member 92 via anchor member 86, anchor member 86 may be disengaged to detach lead body 96 from reinforcement member 92 and allow the lead body to be moved within reinforcement member 92 and deployable lobe member 102 while deployable lobe member 102 and reinforcement member 92 remain fixed within heart 18 of patient 12. Such a configuration may allow lead body 96 to be readjusted within reinforcement member 92, insulating member 94 and deployable lobe member 102, e.g., to further adjust the stimulation field of the electrical stimulation.

In some cases, lead body 96 may be removed entirely from reinforcement member 92, insulating member 94 and deployable lobe member 102 while reinforcement member 92, insulating member 94 and deployable lobe member 102 remained fixed within heart 18 of patient 12. For example, it may be desirable to withdraw lead body 96 along with the one or more conductors within lead body 96 from heart 18 of patient 12 and replace the component with an new lead body/conductors, e.g., if it is determined that the integrity of lead body 96 and/or the conductor(s) within lead body 96 has been diminished in one form or another. In such an example, by leaving reinforcement member 92, insulating member 94 and deployable lobe member 102 fixed within heart 18 of patient 12, after lead body 96 has been removed, the new lead body may be inserted in the proximal end of reinforcement member 92, and guided into a position within heart 18 that is substantially the same as that occupied by lead body 96. Moreover, as the position of aperture 100 is maintained relatively to the adjacent tissue of heart 18 in such a case, the stimulation field produced by the electrical stimulation delivered via the electrode(s) on the new lead body may be substantially the same or similar to that produced by lead body 96. At the least, the position of aperture 100 relative to the adjacent tissue is maintained despite replacing lead body 96 to provide a starting point for adjusting the new lead body within insulating member 94, While the use of lead 90 with deployable lobe member 102 is illustrated in FIG. 8 with regard to implantation of the lead 90 within a coronary vein of heart 18, examples are not limited as such. Rather, such a lead configuration may used to deliver electrical stimulation to any appropriate tissue location of patient 12. In some examples, lead 90 may be positioned epicardially to deliver electrical stimulation to heart 18 of patient 12.

In some example, the proximal portion of the lead body 40 may include one or more visual indicators to orient a clinician to the position of apertures 42 of insulating member 36 relative to the distal portion of lead body 96 and, in particular, electrode 98. For example, the proximal portion lead body 96 may include markings on the outer surface that are positioned on lead body 96 based on the distance between the proximal end of reinforcement member and aperture 100 defined by insulating member 94 to indicate the position of aperture 100 relative to electrode 98. In some example, a proximal portion of reinforcement member 92 may define one or more apertures similar to that of aperture 100 that may be positioned over such a marking to assist a clinician in visualizing the position of aperture 100 relative to electrode 98.

In some examples, lead body 96 may include one or more radial protrusions distributed axially along lead body 96 that receive one or more indentations on the inner surface of reinforcement member 92 and/or insulating member 94. The indented portion(s) of reinforcement member 92 may engage the protrusions on lead body 96 to axially secure reinforcement member 92 at known positions over lead body 96 and/or provide an indication to a clinician the position of reinforcement member 92 and insulating member 94 relative to lead body 96. In some example, the reinforcement member may include the protrusion(s) and the lead body may include the indentation(s).

FIGS. 9A-9C, 10, 11A, 11B, 12A and 12B are conceptual diagrams illustrating examples of insulating member 104 which may be coupled to a reinforcement member (not shown) as described herein.

In FIGS. 9A-9C, insulating member 104 extends axially over the distal portion of lead body 106, which include tip electrode 108 and ring electrodes 110 and 112. Ring electrode 112 in longer than ring electrode 110 in the axial direction, and has a larger overall conductive surface area than ring electrode 110. Insulating member 104 defines apertures 114 and 116. While the axial length of apertures 114 and 116 are substantially the same, the length of aperture 116 is greater than aperture 114 is the radial direction. Accordingly, the opening of aperture 116 is larger than aperture 114.

In FIG. 9A, substantially the entire portion of electrode 110 is covered by insulating member 104 and approximately half of electrode 112 is covered by insulating member 104. As such, approximately half of electrode 112 is exposed by aperture 116 and may conduct electrical stimulation to a tissue of patient 12 (FIG. 1), along with tip electrode 108.

In FIG. 9B, insulating member 104 has been moved axially over lead body 106 toward the proximal end of lead body 106 via the application of force to the reinforcement member (not shown) a distance of $L_1$. In such an orientation, substantially the entire portion of electrode 110 is exposed by aperture 114. Additionally, substantially the entire portion of electrode 112 is exposed by aperture 116. The exposed surfaces of electrodes 110 and 112 may conduct electrical stimulation to adjacent tissue of patient 12.

In FIG. 9C, insulating member 104 has been moved axially over lead body 106 toward the proximal end of lead body 106 via the application of force to the reinforcement member (not shown) a distance of $L_2$. In such an orientation, substantially the entire portion of electrode 110 is exposed by aperture 114. Additionally, approximately half of electrode 112 is exposed by aperture 116 and approximately half of electrode 112 is covered by insulating member 104. The exposed surfaces of electrodes 110 and 112 may conduct electrical stimulation to adjacent tissue of patient 12.

In FIG. 10, insulating member 104 is substantially the same or similar to that shown in FIGS. 9A-9C. However, lead body 106 includes flexible electrode 118 rather than ring electrode 116.

In FIGS. 11A-11B, insulating member 104 is substantially the same or similar to that shown in FIG. 10. Apertures 114 and 116 are approximately the same size. Lead body 106 includes cathodic ring electrodes 120 and 122, and anodic ring electrodes 124 and 126. Cathodic ring electrodes 120 and 122 may be connected in series by a conductor within lead body 106. Similarly, anodic ring electrodes 124 and 126 may be connected in series by a conductor within lead body 106. Insulating member 104 may be moved axially over lead body to expose either electrodes 120 and 124 or electrodes 122 and 126 for bipolar stimulation. In FIG. 11A, electrodes 120 and 124 are exposed by aperture 116 and electrodes 122 and 126 are covered by insulating member 104. In FIG. 11B, electrodes 122 and 126 are exposed by aperture 114 and electrodes 120 and 124 are covered by insulating member 104.

In FIGS. 12A and 12B, insulating member 104 is substantially the same or similar to that shown in FIGS. 11A and 11B. However, insulating member 104 defines aperture 114 on the side of insulating member opposite that which aperture 116 in defined. Similar to that of FIGS. 11A and 11B, lead 106 includes cathodic electrodes 120 and 122, and anodic electrodes 124 and 126. However, electrodes 120, 122, 124, 126 each extend of less than the entire path around circumference of lead body 106. Anodic ring electrodes 124 and 126 may be connected in series by a conductor within lead body 106. Insulating member 104 may be moved axially over lead body to expose either electrodes 120 and 124 or electrodes 122 and 126 for bipolar stimulation. In FIG. 12A, electrodes 120 and 124 are exposed by aperture 116 and electrodes 122 and 126 are covered by insulating member 104. In FIG. 12B, electrodes 122 and 126 are exposed by aperture 114 and electrodes 120 and 124 are covered by insulating member 104.

Various embodiments of the invention have been described. These and other embodiments are within the scope of the following claims.

The invention claimed is:

1. A method of treating a patient condition, comprising:
selectively delivering electrical stimulation therapy to a tissue site of a patient from a medical device via a first selectively exposed portion of at least one electrode of a lead, wherein the lead comprises:
 a lead body including an outer surface, a proximal end, a distal end, and the at least one electrode;
 an electrically insulating member that extends axially over a first portion of the outer surface of the lead body between the proximal end and distal end, the electrically insulating member defining at least one aperture that exposes the first portion of the at least one electrode when in a first position over the lead body; and
 a reinforcement member formed at least partially of a different material than the electrically insulating member and coupled to the insulating member, the reinforcement member extending axially over the outer surface of the lead body between the insulating member and proximal end,
 wherein the reinforcement member comprises an electrically conductive material and is configured to shield the lead body from one or more electromagnetic fields; and
 wherein the reinforcement member surrounds the at least one aperture defined by the insulating member.

2. The method of claim 1, wherein the reinforcement member comprises a braided reinforcement structure that extends over at least a portion of the outer surface of the lead body in the axial direction.

3. The method of claim 2, wherein the braided reinforcement structure comprises braided metallic wires.

4. The method of claim 2, wherein the reinforcement member further comprises a polymeric material, wherein the braided reinforcement structure is at least partially embedded in the polymeric material.

5. The method of claim 1, wherein the at least one electrode comprises a plurality of first electrodes and a plurality of second electrodes, wherein the plurality of first electrodes are electrically coupled in series via a first conductor within the lead body and the plurality of second electrodes are electrically couple in series via a second conductor within the lead body.

6. An implantable lead comprising:
 a lead body including an outer surface, a proximal end, a distal end, and at least one electrode;
 an electrically insulating member that extends axially over a first portion of the outer surface of the lead body between the proximal end and distal end, the electrically insulating member defining at least one aperture that exposes a first portion of the at least one electrode when in a first position over the lead body; and
 a reinforcement member formed at least partially of a different material than the electrically insulating member and coupled to the insulating member, the reinforcement member extending axially over the outer surface of the lead body between the insulating member and proximal end,
 wherein the reinforcement member comprises an electrically conductive material and is configured to shield the lead body from one or more electromagnetic fields; and
 wherein the reinforcement member surrounds the at least one aperture defined by the insulating member.

7. The implantable lead of claim 6 wherein the reinforcement member comprises a braided reinforcement structure that extends over at least a portion of the outer surface of the lead body in the axial direction.

8. The implantable lead of claim 7 wherein the braided reinforcement structure comprises braided metallic wires.

9. The implantable lead of claim 8, wherein the reinforcement member further comprises a polymeric material, wherein the braided reinforcement structure is at least partially embedded in the polymeric material.

10. The implantable lead of claim 6, wherein the at least one electrode comprises a plurality of first electrodes and a plurality of second electrodes, wherein the plurality of first electrodes are electrically coupled in series via a first conductor within the lead body and the plurality of second electrodes are electrically coupled in series via a second conductor within the lead body.

11. An implantable lead comprising:
 a lead body including an outer surface, a proximal end, a distal end, and at least one electrode;
 an electrically insulating member that extends axially over a first portion of the outer surface of the lead body between the proximal end and distal end, the electrically insulating member defining at least one aperture that exposes a first portion of the at least one electrode when in a first position over the lead body; and a reinforcement member formed at least partially of a different material than the electrically insulating member and coupled to the insulating member, the reinforcement member extending axially over the outer surface of the lead body between the insulating member and proximal end; and wherein the reinforcement member comprises braided metallic wires; and wherein the reinforcement member surrounds the at least one aperture defined by the insulating member.

12. The implantable lead of claim 11, wherein the reinforcement member further comprises a polymeric material, wherein the braided metallic wires are at least partially embedded in the polymeric material.

13. The implantable lead of claim 11, wherein the at least one electrode comprises a plurality of first electrodes and a plurality of second electrodes, wherein the plurality of first electrodes are electrically coupled in series via a first conductor within the lead body and the plurality of second electrodes are electrically coupled in series via a second conductor within the lead body.

* * * * *

UNITED STATES PATENT AND TRADEMARK OFFICE
CERTIFICATE OF CORRECTION

| | | |
|---|---|---|
| PATENT NO. | : 8,340,783 B2 | Page 1 of 1 |
| APPLICATION NO. | : 12/825647 | |
| DATED | : December 25, 2012 | |
| INVENTOR(S) | : John L. Sommer et al. | |

It is certified that error appears in the above-identified patent and that said Letters Patent is hereby corrected as shown below:

In the Claims

Col. 22, line 23, delete "are electrically couple in series" and insert in place thereof -- are electrically coupled in series --.

Signed and Sealed this
Seventh Day of October, 2014

Michelle K. Lee
*Deputy Director of the United States Patent and Trademark Office*